(12) United States Patent
Galano-Mangaoang

(10) Patent No.: US 7,919,124 B1
(45) Date of Patent: Apr. 5, 2011

(54) COMPOSITION FOR HAIR GROWTH

(76) Inventor: Margaret Galano-Mangaoang, Seattle, WA (US)

( * ) Notice: Subject to any disclaimer, the term of this patent is extended or adjusted under 35 U.S.C. 154(b) by 25 days.

(21) Appl. No.: 12/290,584

(22) Filed: Oct. 31, 2008

(51) Int. Cl.
*A01N 65/00* (2009.01)
(52) U.S. Cl. ..................................................... 424/725
(58) Field of Classification Search .................. None
See application file for complete search history.

(56) References Cited

U.S. PATENT DOCUMENTS

| | | |
|---|---|---|
| 4,777,039 A | 10/1988 | Lang et al. |
| 5,215,760 A | 6/1993 | Kavoussi et al. |
| 5,587,174 A | 12/1996 | Lang et al. |
| 5,695,748 A | 12/1997 | Francis |
| 5,827,510 A | 10/1998 | Mesquitta |
| 6,465,514 B1 | 10/2002 | Hallam et al. |
| 6,551,606 B1 | 4/2003 | Golz-Berner et al. |
| 7,025,955 B2 | 4/2006 | Siddiqui et al. |

*Primary Examiner* — Michael V Meller
(74) *Attorney, Agent, or Firm* — Montgomery Patent and Design LLC; Robert C. Montgomery

(57) ABSTRACT

The invention as presently conceived discloses a compound of *Aloe vera* oil and coconut oil to improve the scalp region and to reinvigorate hair growth. The active ingredients are mixed in a formulaic blend for immediate use or packaged for subsequent use. The active ingredients are prepared in an all-natural and unprocessed method of preparation. A user would apply a small amount to their scalp every day, wherein it absorbs thereinto the scalp.

8 Claims, No Drawings

COMPOSITION FOR HAIR GROWTH

RELATED APPLICATIONS

The present invention was first described in Disclosure Document No. 609,995 filed on Dec. 7, 2006 with the United States Trademark and Patent Office.

FIELD OF THE INVENTION

The present invention relates to a topical hair treatment composition and more particularly, to an all natural composition of emulsifiers and an emollient to improve a scalp region and to reinvigorate hair growth that is applied to the scalp everyday and improves the health of hair and scalp of a user.

BACKGROUND OF THE INVENTION

Many people suffer from hair loss. While many choose to just live with the condition and view it as a sign of maturity, wisdom or handsomeness, many choose to combat it, as witnessed by the various topical medicines on the market today. However, these medicines are relatively expensive, and must be used continuously to be effective. Additionally some of these medicines can have unpleasant and/or dangerous side effects. Other options are masking the hair loss by using wigs, toupees, hair weaves, hair plugs and the like. Most of these products, however, suffer from drawbacks in that they are either overly obvious, are overly expensive or simply just do not look natural and fail to produce naturally looking hair. Accordingly, there exists a need for a means by which one can combat thinning and/or balding hair with a composition for from all natural ingredients that is unrefined or processed using dangerous chemicals without the disadvantages as listed above.

Several attempts have been made in the past to develop and patent a composition of promoting hair growth. U.S. Pat. No. 7,025,955 issued to Siddiqui discloses a method for maximizing scalp health and inducing enhanced visual and tactile hair quality. This patent does not appear to disclose a composition for hair growth comprising *Aloe vera*, guava (*Psidium var.*) and coconut oil (*Cocos nucifera*).

U.S. Pat. No. 6,551,606 issued to Golz-Berner and Zastrow discloses a cosmetic product containing enzymes. This patent does not appear to disclose a composition for hair growth comprising *Aloe vera*, guava (*Psidium var.*), and coconut oil (*Cocos nucifera*).

U.S. Pat. No. 6,465,514 issued to Hallam and Robinson discloses methods and compositions for the promotion of hair growth. This patent does not appear to disclose a composition for hair growth comprising *Aloe vera*, guava (*Psidium var.*) and coconut oil (*Cocos nucifera*).

U.S. Pat. No. 5,827,510 issued to Mesquitta discloses a hair growth preparation. This patent does not appear to disclose a composition for hair growth with the same agents as the instant invention.

U.S. Pat. No. 5,695,748 issued to Francis discloses a composition and process for the treatment and restoration. This patent fails to disclose a composition for hair growth utilizing the same agents as the instant invention.

U.S. Pat. No. 5,215,760 issued to Kavoussi and Kavoussi discloses a saturated solution of purified sodium chloride in purified *aloe vera* for inducing and stimulating hair growth and for decreasing hair loss. This patent fails to disclose a composition for hair growth that contains guava (*Psidium var.*) or coconut oil (*Cocos nucifera*).

U.S. Pat. No. 5,587,174 issued to Lang et al. discloses a cosmetic composition for treating skin and hair containing apple wax and methods of making them. This patent does not appear to disclose a composition for hair growth that contains guava (*Psidium var.*) or *Aloe vera*.

U.S. Pat. No. 4,777,039 issued to Lang et al. discloses a pearlescent hair conditioning composition. This patent does not appear to disclose a composition for hair growth that contains guava (*Psidium var.*) or *Aloe vera*.

None of the prior art particularly describes a composition for hair growth that comprises solely of all-natural ingredients. Accordingly, there is a need for a composition for hair growth comprised of all-natural ingredients, wherein said composition has been unrefined or un-processed and free of dangerous chemicals.

SUMMARY OF THE INVENTION

In view of the foregoing disadvantages inherent in the prior art, it has been observed that there is need for a safe all-natural composition for hair growth, wherein said composition has been unrefined or unprocessed.

It is an object of the composition for hair growth to comprise a hair follicle regenerating and soothing oil composition for topical application to a user.

Another object of the composition provides a method of use comprising an application thereto a user's scalp to regenerate damaged or dormant hair follicles contained therein the scalp tissues.

It is a further object of the composition for hair growth to provide such a formulation that is readily absorbed into the scalp tissue.

It is another object to provide an essential composition comprising a formulaic aqueous mixture of an emulsifier and an emollient.

It is an aspect of the essential composition to further comprise Aloe vera and guava (*Psidium var.*) as the emulsifier.

It is another aspect of the essential composition to comprise coconut oil as the emollient.

A method for utilizing the composition for hair growth may be accomplished by performing the following steps: adding a cleanser agent such as baby shampoo or Aloe vera shampoo prior to application of the essential composition to the user's scalp tissue; massaging the essential composition thoroughly into the user's scalp; allowing the treatment with the essential composition to remain on the scalp for a minimum of thirty (30) minutes or as long as over-night; removing the essential composition from the scalp if desired, using normal shampoo and enjoying the benefits of the composition for hair growth.

DETAILED DESCRIPTION OF THE PREFERRED EMBODIMENT

The best mode for carrying out the invention is presented in terms of its preferred embodiment. However, the invention is not limited to the described embodiment and a person skilled in the art will appreciate that many other embodiments of the invention are possible without deviating from the basic concept of the invention, and that any such work around will also fall under scope of this invention. It is envisioned that other styles and configurations of the present invention can be easily incorporated into the teachings of the present invention, and only one particular configuration shall be shown and described for purposes of clarity and disclosure and not by way of limitation of scope.

The terms "a" and "an" herein do not denote a limitation of quantity, but rather denote the presence of at least one of the referenced items.

The invention herein refers to a chemical composition resulting in a balm for application to a user's scalp.

The term "balm" herein refers to an all-natural composition such as a liniment, lotion, or any other topical preparations for application to the skin or scalp of a user.

The term "emollient" herein refer to any composition or a property thereof any composition that is hygroscopic and prevents dryness and otherwise moisturizes the application area.

The term "all-natural" herein refers to components of the present composition that have been extracted or otherwise derived from naturally occurring sources that are unrefined or unprocessed.

The essential composition of the present invention comprises a hair follicle regenerating and soothing oil composition for the topical application to a user. Preferably, the topical composition is to be applied to a user's scalp to regenerate damaged or dormant hair follicles contained therein the scalp tissues. The essential composition is a formulation of all-natural products that have been unrefined or unprocessed, and is readily absorbed into the scalp tissue of the user.

Typically, the preferred essential composition of the present invention involves the formulaic aqueous mixture of an emulsifier and an emollient.

More specifically, the preferred essential composition of the present invention comprises a formulaic blend of *Aloe vera* and guava (*Psidium var.*) as an emulsifier, and coconut oil as the emollient.

An example of a preferred essential composition of the present invention is prepared a follows:

| Component | Amount (Vol %) |
| --- | --- |
| Coconut oil (*Cocus nucifera*) | 70 |
| Aloe vera | 20 |
| guava (*Psidium* var.) | 8 |
| Distilled water | 2 |

It is envisioned that other styles and configurations of the present invention can be easily incorporated into the teachings of the present invention, and only one particular configuration shall be shown and described for purposes of clarity and disclosure and not by way of limitation of scope.

Method of Preparation and Usage Thereof the Essential Composition

The preferred embodiment of the present invention can be utilized by the common user in a simple and effortless manner with little or no training. The preparation and processing of individual ingredients may be achieved by performing the following steps:

1. Coconut Oil (*Cocus nucifera*) Preparation—Using ten (10) coconuts, extract the milk from coconuts and place in a large bowl. Grate the coconut meat and place the resulting meat pulp also in the large bowl. Add two (2) cups of distilled water to the large bowl. Manually mash the contents of the large bowl to produce coconut milk. Strain the milk into a pot for cooking. Heat the pot to bring the milk to a boil while stirring occasionally. The solution will separate out into light brown curds (solids) and a watery extract (coconut oil). Strain the coconut oil solids from the surface of coconut oil solution and place the coconut oil solution into a bowl. Set aside.

2. *Aloe Vera* Preparation—Using ten (10) medium size *Aloe vera* leaves, remove any sharp edges from the *Aloe vera* leaves. Crush the *Aloe vera* leaves and set them aside.

3. Final Preparation—Heat the coconut oil solution over a burner until a light boil, stirring occasionally. Add seventy (70) guava (*Psidium var.*) leaves. Add the prepared *Aloe vera* leaves. Apply heat to the mixture for a few more minutes until the guava (*Psidium var.*) leaves turn a brown color. Remove the guava (*Psidium var.*) leaves. Continue applying heat for a few minutes until the *Aloe vera* oil is extracted. The mixture should turn a yellow-green color. Strain off the essential composition from the mixture into a new container, allowing the essential composition to cool. The essential composition is now ready for packaging or use.

The essential composition is envisioned to be purchased in most natural food health stores or where consumer care products are typically sold. After initial purchase of the essential composition, preparation is envisioned to take place as follows: warming the essential composition prior to application thereon a user's scalp; massaging the essential composition thoroughly into the user's scalp; allowing the treatment with the essential composition to remain on the scalp for a minimum of thirty (30) minutes or as long as overnight; and, removing the essential composition from the scalp if desired, using normal shampoo.

The proper and effective use of the essential composition provides a hair follicle regenerating balm that does not contain any added chemicals; remains visually undetected on the scalp; and is readily absorbed into the scalp tissues.

Additionally, the essential composition may be applied thereto any desired skin surface to act as a balm or hair growth promoter.

The foregoing descriptions of specific embodiments of the present invention have been presented for purposes of illustration and description. They are not intended to be exhaustive or to limit the invention and method of use to the precise forms disclosed. Obviously many modifications and variations are possible in light of the above teaching. The embodiment was chosen and described in order to best explain the principles of the invention and its practical application, and to thereby enable others skilled in the art to best utilize the invention and various embodiments with various modifications as are suited to the particular use contemplated. It is understood that various omissions or substitutions of equivalents are contemplated as circumstance may suggest or render expedient, but is intended to cover the application or implementation without departing from the spirit or scope of the claims of the present invention.

What is claimed is:

1. A method of preparing a composition for promoting hair growth and scalp health comprising the following steps:
   preparing an emulsifier containing guava or *Aloe Vera;*
   preparing an emollient containing coconut oil;
   combining said emulsifier and emollient into a mixture;
   heating said mixture within a cooking vessel over a heat source;
   stirring said mixture occasionally until said mixture becomes an intermediary composition;
   applying heat to said intermediary composition for a few more minutes and removing said intermediary composition from said heat source, thereby resulting in an intermediary composition and an essential composition wherein the essential composition has an oil-like consistency which floats on the surface of the intermediary composition;
   removing said essential composition from said intermediary composition;

transferring said essential composition to a container; and, permitting said essential composition to cool.

2. The method of claim 1, wherein said emulsifier comprises a first emulsifier and a second emulsifier, and further comprising preparing a formulaic blend of about 20% by volume of said first emulsifier, about 8% by volume of said second emulsifier, about 2% of distilled water, and about 70% by volume of said emollient.

3. The method of claim 2, further comprising the steps of inverting said container with said essential composition onto a palm such that a usable amount of said essential composition is dispensed;

warming said essential composition prior to application thereof;

applying said usable amount of essential composition onto a scalp;

thoroughly massaging said usable amount of essential composition into said scalp;

permitting said usable amount of essential composition to remain on said scalp for at least thirty (30) minutes;

removing any remaining amount of said essential composition from said scalp; and, reusing said essential composition as necessary to promote hair growth and scalp health.

4. The method of claim 2, further comprising the step of: applying said essential composition onto a desired skin surface.

5. The method of claim 3, wherein said step of preparing said emollient comprises preparing a coconut oil composition, further comprising the steps of:

extracting milk from about ten coconuts into a large container;

removing coconut meat therefrom said about ten coconuts;

grating said coconut meat to gather coconut meat pulp;

placing said coconut meat pulp into said large container;

adding about two cups of distilled water thereto said large container;

manually mashing said coconut meat pulp and said about two cups of distilled water to produce a coconut milk mixture;

straining said coconut milk mixture into said cooking vessel;

heating said cooking vessel to bring said coconut milk mixture to a boil while stirring occasionally; and, straining coconut oil solids from a surface of said coconut milk mixture, thereby producing said coconut oil composition and placing into a separate container for subsequent use.

6. The method of claim 3, wherein said first emulsifier is Aloe Vera and said second emulsifier is guava which are made by the steps of:

obtaining about ten medium sized *Aloe vera* leaves;

removing any sharp edges from said *Aloe vera* leaves to achieve an amount of said *Aloe vera* leaves;

setting aside said amount of *Aloe vera* leaves for subsequent use;

obtaining about seventy guava leaves and setting aside for subsequent use.

7. The method of claim 6, wherein said step of becoming an intermediary composition comprises observing a brown color of said guava leaves.

8. The method of claim 7, wherein said step of removing said essential composition from said intermediary composition comprises straining.

\* \* \* \* \*